United States Patent [19]

Griffiths et al.

[11] 4,147,051

[45] Apr. 3, 1979

[54] DENSIMETER

[75] Inventors: John S. Griffiths, Ottawa; Roger N. Stone, Stittsville, both of Canada

[73] Assignee: Sharon Electronics Limited, Ottawa, Canada

[21] Appl. No.: 809,037

[22] Filed: Jun. 22, 1977

[51] Int. Cl.² ............................................. G01N 9/30
[52] U.S. Cl. .............................. 73/32 R; 250/231 SE
[58] Field of Search ...................... 73/32 R, 32 A, 434; 250/231 SE

[56] References Cited

U.S. PATENT DOCUMENTS

| | | | |
|---|---|---|---|
| 2,999,380 | 9/1961 | Thiessen et al. | 73/32 R |
| 3,723,011 | 5/1973 | Flory et al. | 250/231 SE |
| 3,814,934 | 6/1974 | Mesh et al. | 250/231 SE |
| 3,902,063 | 8/1975 | Oelsch et al. | 250/231 SE |

Primary Examiner—Stephen A. Kreitman
Attorney, Agent, or Firm—Smart & Biggar

[57] ABSTRACT

A densimeter for measuring the density of liquids is disclosed. The densimeter comprises a substantially vertical shaft having a central axis. The densimeter further comprises means for rotating the shaft about its axis and a vessel mounted on the shaft asymmetrically with respect to the shaft axis. Counterbalancing means are provided on the shaft for at least partly compensating for the asymmetry. The shaft is resiliently mounted with freedom of oscillation transverse to the shaft axis. Means are provided for measuring the amplitude of the oscillations.

17 Claims, 9 Drawing Figures

FIG. 6 PHASE COMPARATOR WAVEFORMS

FIG. 7

VOLTAGE/PHASE CHARACTERISTIC FOR
PHASE COMPARATOR/FILTER COMBINATION

FIG. 8

DENSIMETER

GENERAL DESCRIPTION, DISCUSSION OF PRIOR ART AND OBJECTS OF THE INVENTION

This invention relates to apparatus for continuously measuring the density of liquids or liquids having a fine suspension.

A density measuring apparatus, commonly known as a densimeter is known from Canadian Pat. No. 605,318 which issued on Sept. 20, 1960 in the name of G. J. Thiessen and I. R. Dagg. In this prior art densimeter a system containing a liqiud sample is rotated about a reference axis and the extent of the resulting imbalance, i.e. the amplitude of the oscillations from the reference axis is measured. The value obtained is linearly related to the deviation from the value of the known specific gravity of a reference sample which when used in the system causes the system to be balanced. The amplitude of the oscillations is measured in the prior system by measuring the voltage induced by an electromagnet in a coil which is physically attached to the rotating system.

The prior densimeter suffers from the disadvantage that it is only capable of measuring the density of a descrete sample contained in a vessel and is incapable of continuously measuring the density of a continuously flowing liquid. Furthermore, the means for measuring the amplitude of the oscillations is not highly accurate.

A continuous flow densimeter is known from an article published in the Pulp Paper Magazine Canada 60, No. 9: T263-T268 (Sept. 1959) by G. J. Thiessen and I. R. Dagg and entitled "Vibration as a Measure of Liquid Density and Pulp Stock Consistency". According to this system, fluid is pumped in through one end of a hollow shaft and exhausted from the other end after passing through an asymmetrically disposed vessel. A liquid seal bearing is required at both ends of the shaft. Due to the lateral displacement of the upper end of the shaft, the upper end of the shaft is connected to the external circulation by means of flexible bellows.

The prior continuous flow densimeter has not been developed commercially probably because the flexible bellows is only satisfactory under conditions of very low pressure.

It is an object of the present invention to improve the accuracy of prior densimeters, which may be discrete sample densimeters or continuous flow densimeters, by incorporating improved oscillation measuring means.

It is also an object of the present invention to improve the prior continuous flow densimeter by dispensing with the liquid seal and bellows at the upper end of the shaft thus increasing the liquid pressure capability and the accuracy of the system.

From a first aspect, the present invention provides a densimeter comprising a substantially vertical shaft having a central axis, means for rotating the shaft about its axis, a vessel for containing a liquid sample mounted on the shaft asymmetrically with respect to the shaft axis, counterbalancing means for at least partly compensating for the assymetry, the shaft being resiliently mounted with freedom of oscillation transverse to the axis, and means for measuring the amplitude of the oscillations, said measuring means including two radiation paths each of which comprises a source and a detector, a shutter carried by the shaft and disposed to interrupt the radiation paths to generate two waveforms as the shaft rotates and means for detecting a shift in phase between the two waveforms, whereby the phase shift is proportional to the amplitude of the oscillations which, in turn, is proportional to the deviation of the specific gravity of the sample from a reference value.

From a second aspect, the present invention is a continuous flow densimeter comprising a substantially vertical shaft having a central axis, means for rotating the shaft about the central axis, a vessel mounted on the shaft asymmetrically with respect to the shaft axis, counterbalancing means on the shaft for at least partly compensating for the asymmetry, the shaft being resiliently mounted with freedom of oscillation transverse to the shaft axis, and means for measuring the amplitude of the oscillations, the shaft comprising two concentric tubes, the inner tube communicating with the interior of the vessel and the space between the two tubes communicating with the interior of the vessel, the shaft being adapted to permit fluid to be pumped through the vessel via the shaft whereby the outlet flow of fluid along the shaft is counter to and separate from the inlet flow.

BRIEF DESCRIPTION OF THE DRAWINGS

The invention will now be described in detail with reference to the accompanying drawings, in which.

DESCRIPTION OF THE PREFERRED EMBODIMENTS

Figure 1:
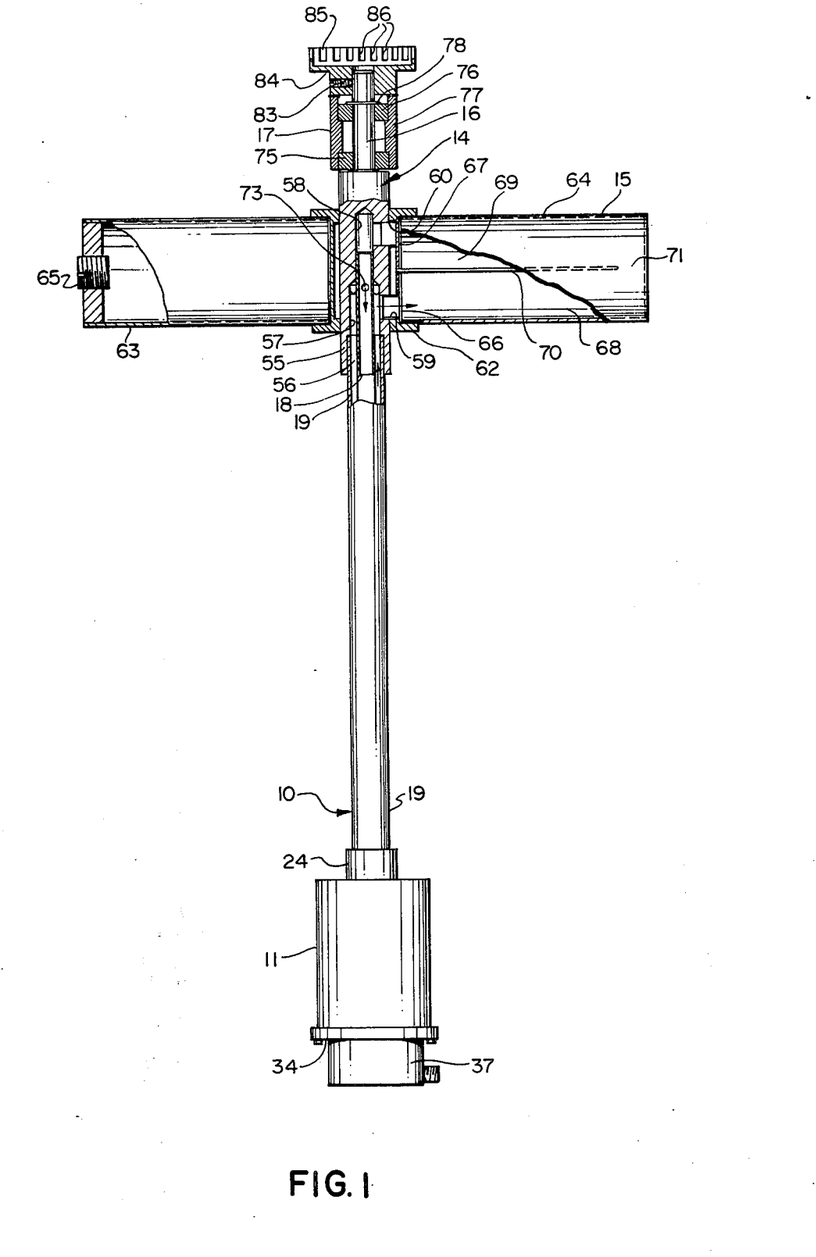
FIG. 1 is a side elevational view of a densimeter spindle according to the present invention, partially in section at its upper portion.
Figure 2:
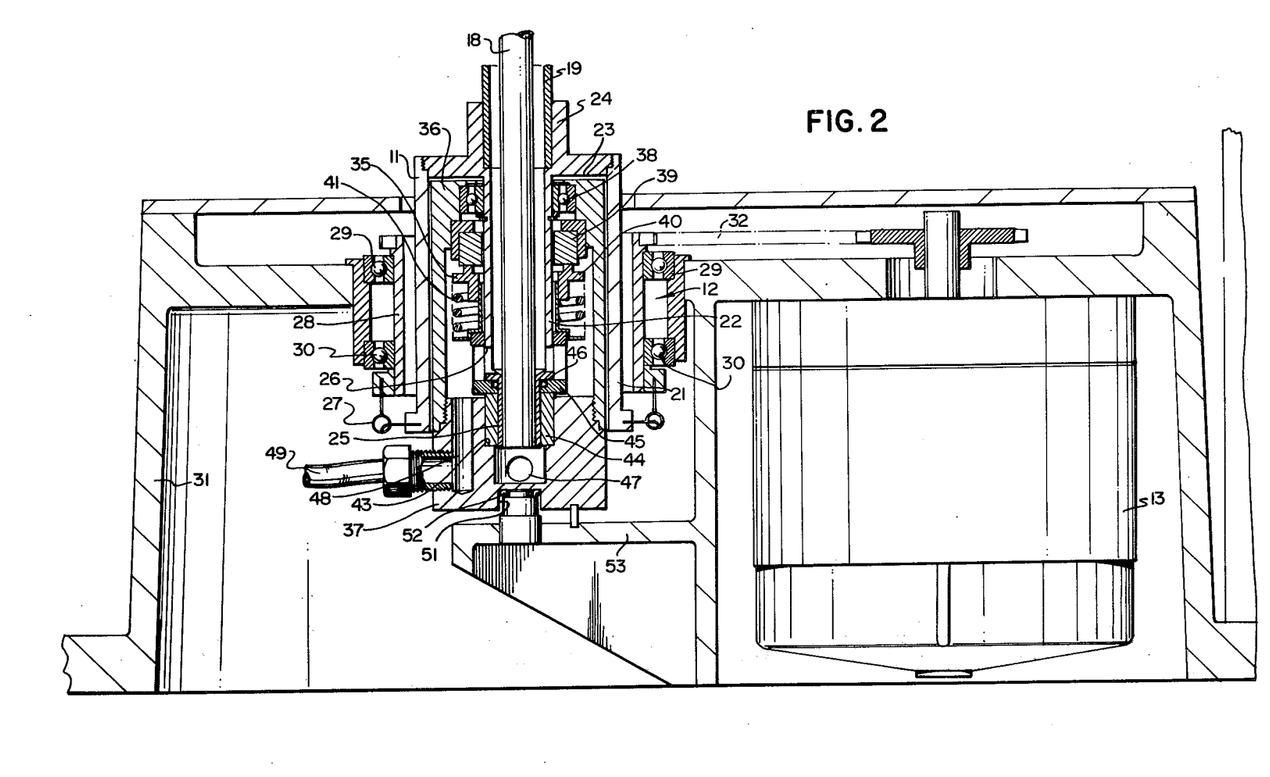
FIG. 2 is a partial side elevation of the apparatus frame and spindle, also partially in section.

Referring to FIGS. 1 and 2, the densimeter includes a vertical hollow shaft 10 which carries on its lower end a tubular member 11 which is journalled in a lower bearing assembly 12 snd which is adapted to be driven by an electric motor 13. The shaft 10 carries on its upper end a subassembly 14 which includes a transverse rotor tube 15 and a vertically extending shaft 16 journalled in an upper bearing assembly 17.

The shaft 10 comprises two concentric tubes 18 and 19, the inner tube 18 projecting beyond the outer tube 19 at each end of the shaft 10.

The tubular member 11 comprises two concentric tubular portions 21 and 22 projecting downwardly from a flange portion 23, and a tubular portion 24 projecting upwardly from the flange portion 23. The diameter of the tubular portion 24 is slightly greater than that of the outer tube 19 so as to be able to receive the lower end of the outer tube 19 as can best be seen in FIG. 2. The inner tube 18 is received through the tubular portion 22. The diameter of the tubular portion 22 is over most of its length approximately equal to the diameter of the outer tube 19 but at its lower end portion 25 the diameter decreases to slightly greater than the diameter of the inner tube 18 so as to be able to receive the lower end of the inner tube 18. The tubular portion 24, the lower end portion 25 and corresponding portions of the outer and inner tubes 19 and 18, respectively, are threaded to secure the shaft 10 to the tubular member 11. The tubular portion 22 of the member 11 is provided with a plurality of through holes 26 spaced circumferentially around the lower part of its larger diameter portion.

The outer tubular portion 21 is connected by means of a drive spring 27 to a tubular drive shaft 28 which encircles the outer tubular portion 21. The drive shaft 28 is mounted for rotation on two spaced bearings 29 and 30 mounted in a base housing 31, and is arranged to be driven by the electric motor 13 via a belt 32.

Figure 4:
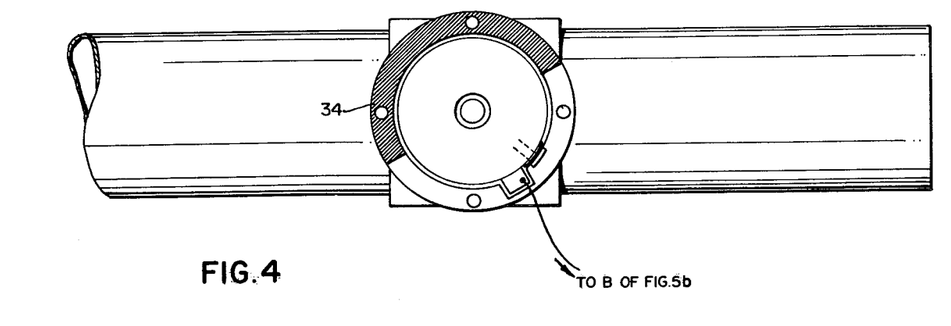
FIG. 4 is a bottom plan view of the densimeter of FIG. 1.

As can be seen in FIG. 4, the lower end flange 34 of the tubular portion 21 is divided into equal black and white portions the purpose of which will be described below.

Located primarily in the space between the tubular portions 21 and 22 is a seal assembly 35. This comprises an upper seal housing 36 threadably connected to a lower seal housing 37. The upper seal housing 36 carries a bearing 38 which supports rotatably the inner tubular portion 22 of the member 11. The upper seal housing also carries a stationary ceramic sealing ring 39 against which a rotatable carbon graphite sealing ring 40 is urged by means of a coil spring 41 mounted on the inner tubular portion 22.

The lower seal housing 37 comprises a stepped central recess 43 the upper part of which receives a graphite bushing 44 through which passes the portion 25 of the inner tubular portion 22. A thrust ring 45 carried on the portion 25 and sealed with respect to the portion 25 by means of an O-ring 46 sealingly engages the upper edge of the graphite bushing 44. The lower part of the recess 43 communicates by means of an aperture 47 with the outer surface of the lower sealing housing 37. A flexible outlet hose (not shown) may be plugged into this aperture 47. A dog leg aperture 48 through the lower seal housing 37 interconnects a flexible inlet hose 49 with the space between the tubular portion 22 and the upper seal housing 36 immediately adjacent the through holes 26 in the portion 22.

The lower seal housing 37 has a central recess 51 on its lower face and this recess seats on a pivot 52 projectingly upwardly from a portion 53 of the base housing 31. The lower seal housing 37 and the portion 53 of the base housing are keyed to prevent rotation of the housing 37.

The sub-assembly 14 carried on the upper end of the shaft 10 includes a tube 55 which has a stepped bore which progresses, from the bottom, from a relatively wide portion 56 via a narrower portion 57 to the narrowest portion 58. The upper end of the outer tube 19 of shaft 10 is received in force-fit in the wide portion 56 of the bore and the upper end of the inner tube 18 is received in force-fit in the narrowest portion 58. Two axially spaced holes 59 and 60 communicate, respectively, with the portions 57 and 58 and also with the outer surface of the tube 55.

Secured to the outer surface of the tube 55 is a hub 62 which carries the transverse rotor tube 15. The rotor tube comprises two halves of similar external dimensions extending laterally from diametrically opposed positions on the hub 62, one half 63 being simply a counterweight to the other half 64 which is adapted to receive the fluid being measured. The half 63 has an adjustable screw 65 at its outer end surface for balancing with the half 64. The half 64 has openings 66 and 67 aligned, respectively, with the axially spaced holes 59 and 60 of the tube 55. The openings 66 and 67 communicate with respective equal compartments 68 and 69 formed in the half 64 by a baffle plate 70 which extends along a horizontal plane from the inner end surface to a position short of the outer end surface to define a passage 71 joining the compartments 68 and 69. Several small air bleed holes 73 are provided in the upper end portion of the end portion of inner tube 18 adjacent the bore portion 57.

The shaft 16 is formed on the upper end of the tube 55 and is rotatably received in the bearing assembly 17 which comprises two bearings 75 and 76 spaced in a housing 77. A circlip 78 secures the bearing assembly 77 vertically on the shaft 16. The bearing housing 77 is resiliently mounted to a transverse mounting plate 79 by an arrangement of springs seen in FIG. 3. The arrangement of springs includes two parallel spaced leaf springs 80 which are connected at one end to the bearing housing 77 and at the other end to a shaft 81 extending parallel to the springs 80. Two leaf springs 82 are connected to opposite ends of the shaft 81, the springs extending in opposite directions from the shaft at right angles to the shaft and are bolted to the mounting plate 79. This arrangement permits 360° lateral movement of the bearing assembly 77.

With reference to the upper portion of FIG. 1, a drum member 84 is attached to the extreme upper end of shaft 16 by a set screw 83. The drum member 84 has an axially extending rim 85 provided with 36 equi-spaced slots 86. It should be understood that the number of slots provided in the drum is important to the particular embodiment described here but is not important to other embodiments. The number of slots is therefore not intended to limit the scope of the present invention.

A printed circuit board (not shown) can be mounted over the upper free end of the drum 84 so that two light emitting diodes (LED) 87 (see FIG. 5a) are positioned in the space defined by the rim 85 and two diametrically opposed photosensitive field effect transistors (photofets) 88, are positioned outside the rim 85 within the beams of the respective LED's. The two LED's and the two photofets are therefore aligned in a plane normal to the longitudinal axis of the spindle, when the spindle is at rest. As the drum is rotated the beams from the LED's reach their respective photofets only when a slot 86 is aligned with the LED and the photofet. The light patterns at the photofets, caused by the interruption of the beams are translated into two electrical pulse trains by the photofets and the phase relationship between these two electrical waveforms is measured.

If the spindle rotates concentrically, i.e. without deviating from its longitudinal rest axis, the phase relationship between the two waveforms remains stable. However, if the axis of the shaft 10 is moved laterally with respect to the light beams, on light waveform is advanced in time and the other is retarded in time. The shift in phase of the two waveforms corresponds to a lateral shift of the shaft axis with respect to the longitudinal rest axis.

Figures 5A, 5B:
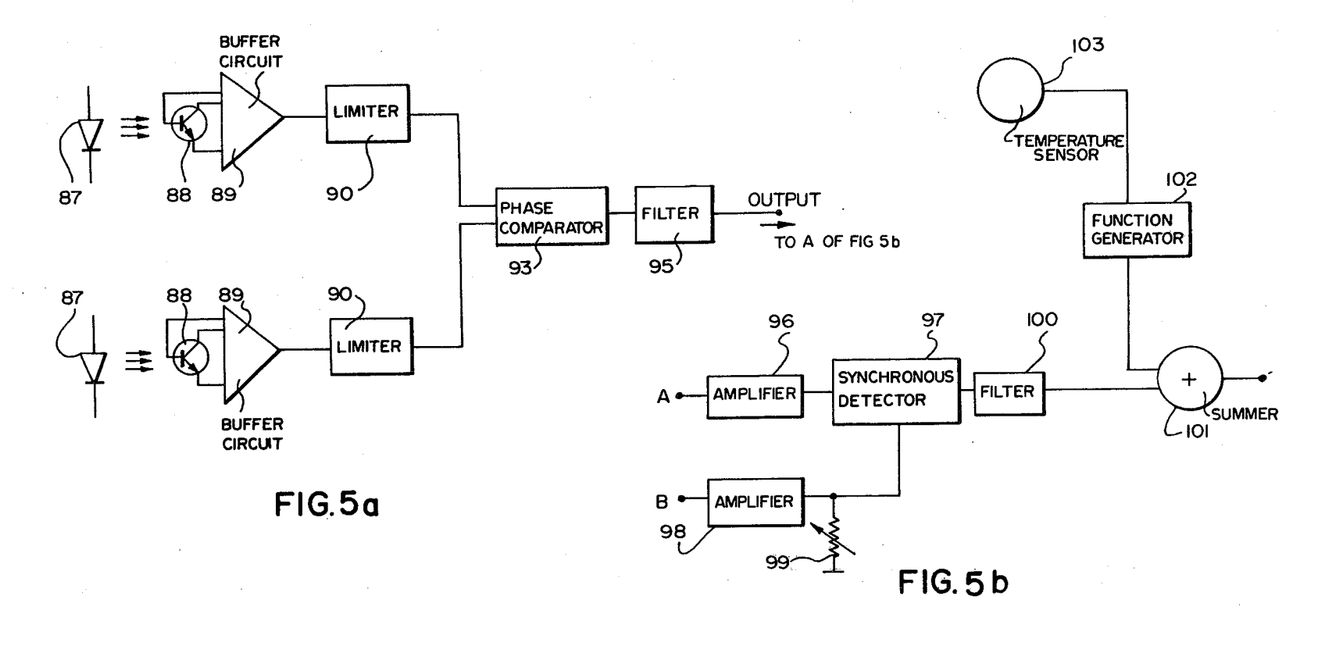
FIG. 5a is a block diagram of the electrical circuitry used in a sensing head of the densimeter.
FIG. 5b is a block diagram of the electrical circuitry used to demodulate the output from the sensing head.
Figure 6:
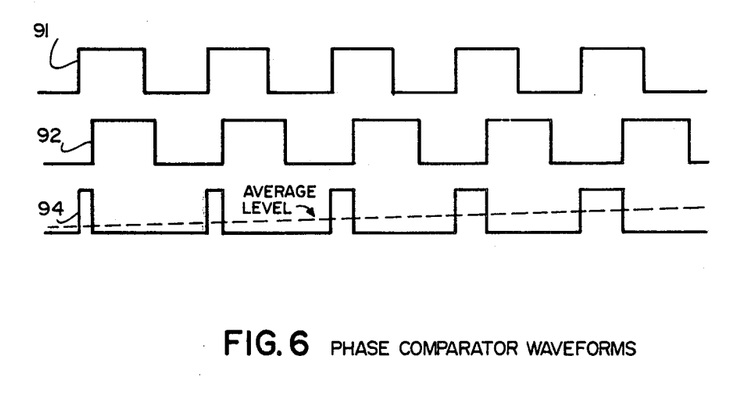
FIG. 6 is a diagram showing waveforms derived at different points in the electrical circuitry of the sensing head.
Figure 7:
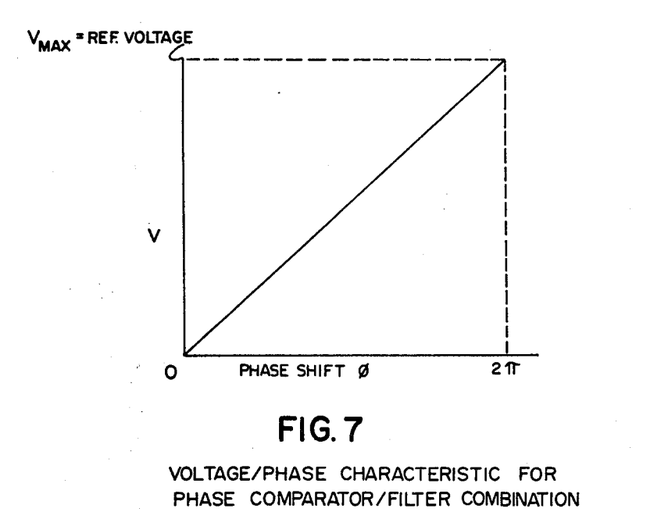
FIG. 7 is a diagram showing the voltage phase characteristic for a phase comparator portion of the sensing head.

With reference to FIG. 5a, the electrical waveforms derived by the photofets 88 are passed through buffer circuits 89 and then limiters 90 which produce square waveforms 91 and 92 as shown in FIG. 6. These square waveforms are synchronous with the light waveforms initially produced. The output signals from the limiters 90 are fed to a comparator 93 in which the leading edge of one train of square waves is used to set a flip-flop. The leading edge of the other train of square waves is used to reset the flip-flop. The time intervals which the flip-flop spends in the "set" state are proportional to the delay between the respective leading edges of the two square wave pulse trains. The resulting waveform 94 (FIG. 6) has an average value or "d.c. content" proportional to the delay or phase difference. Thus, if a plot is drawn (FIG. 7) of the average value V of the waveform versus phase difference $\phi$ the result is a straight line.

If the phase difference increases past 360° it effectively becomes zero again as does the output voltage from the phase comparator 93. Such a condition is difficult to detect and so the sensor is mechanically adjusted to ensure that the sensor operates within the characteristic of FIG. 7 i.e. the phase difference does not go beyond 360°.

The output of the comparator 93 is passed through a low pass filter 95 having a cut-off frequency of 24 Hz for filtering out noise but permitting passage of the output signal which has a fundamental frequency at 18 Hz, the speed of rotation of the spindle.

With reference to FIG. 5b, the output of the low pass filter 95 is fed through and amplifier 96 to a synchronous detector 97. A reference square wave generated by a photodiode (not shown) exposed to the black and white portions of the end flange 34 of the tubular portion 22, see FIG. 4, is now amplified in an amplifier 98 and also fed to the synchronous detector 97. A phase preset adjuster 99 is provided to ensure that the reference voltage is in phase with the detected signal. The output of the synchronous detector 97 is fed through a low pass filter 100 to one input of a summer 101. Another input of summer 101 is fed by a function generator 102 supplied by a temperature sensor 103. The temperature sensor may be located in the shaft 10 and derives a voltage which varies linearly with temperature changes. The object of the function generator 102 is to produce a voltage which more closely corresponds to the variation in specific gravity due to temperature change. The output from the summer 101 is a voltage which linearly represents the specific gravity of the fluid being measured corrected for temperature.

The densimeter may be calibrated by rotating the shaft 10 at a predetermined speed, for example 18 revs/second and pumping a quantity of reference fluid at a predetermined temperature and of known constant specific gravity via inlet 49, through the holes 26 of the annular space between the pipes 18 and 19, through the hole 59 into the compartment 68, through the passage 71 into the compartment 69, though the hole 60 and back down the center pipe 18 to the outlet hose. The screw 65 is adjusted to provide balance. This sequence is repeated using a sample which has a density which is known to be higher than that of the reference by a known amount, except that the screw 65 is not adjusted.

The imbalance causes the shaft 10 and the drum 84 to oscillate about their axis of rotation. This gives rise to a phase difference between the waveforms generated by the photofets 88, this phase difference deriving a voltage 94 at the output of the comparator 93 corresponding linearly to the shift of the axis of shaft 10 and thus to the deviation in specific gravity of the fluid from the value of the first sample. This signal 94 is passed via filter 95 and amplifier 96 through the synchronous detector 97 together with the reference signal so that the output is a full-wave rectified signal which after low pass filtering in the filter 100 produces a DC output, of say 5 volts, which is proportional to the deviation in specific gravity of the fluid. As the fluid is at the desired predetermined temperature, no correction signal from the temperature sensor appears at the summer and so the output of the summer is the same as its input. A scale may now be marked off between 0 and 5 volts to represent the deviation in the specific gravity from a reference value.

It was found during test that bearing wear or normal bearing clearence could affect the ultimate reading producing a dead band at near perfect balance. Accordingly, more accurate results are achieved when a small imbalance is introduced instead of obtaining complete balance when the densimeter is calibrated using the reference fluid, so that all measurements were relative to this imbalance. The resulting zero to 5 volt signal representing the change in specific gravity from the reference value must, of course, be compensated by introducing a small opposing voltage representing the original imbalance.

Figure 3:
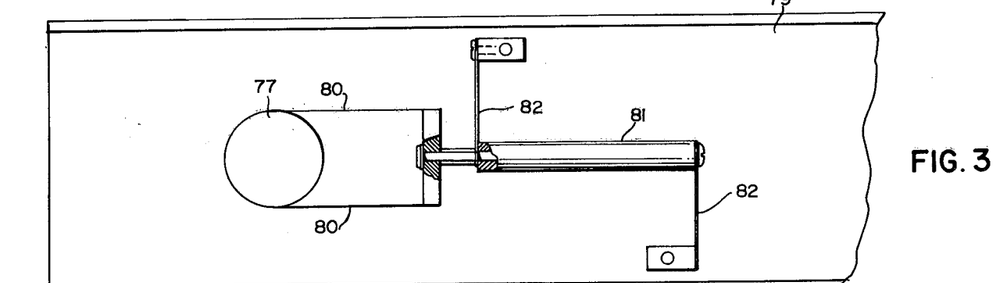
FIG. 3 is a top plan view showing the resilient mounting of the spindle to the frame of the densimeter of FIG. 1.
Figure 8:
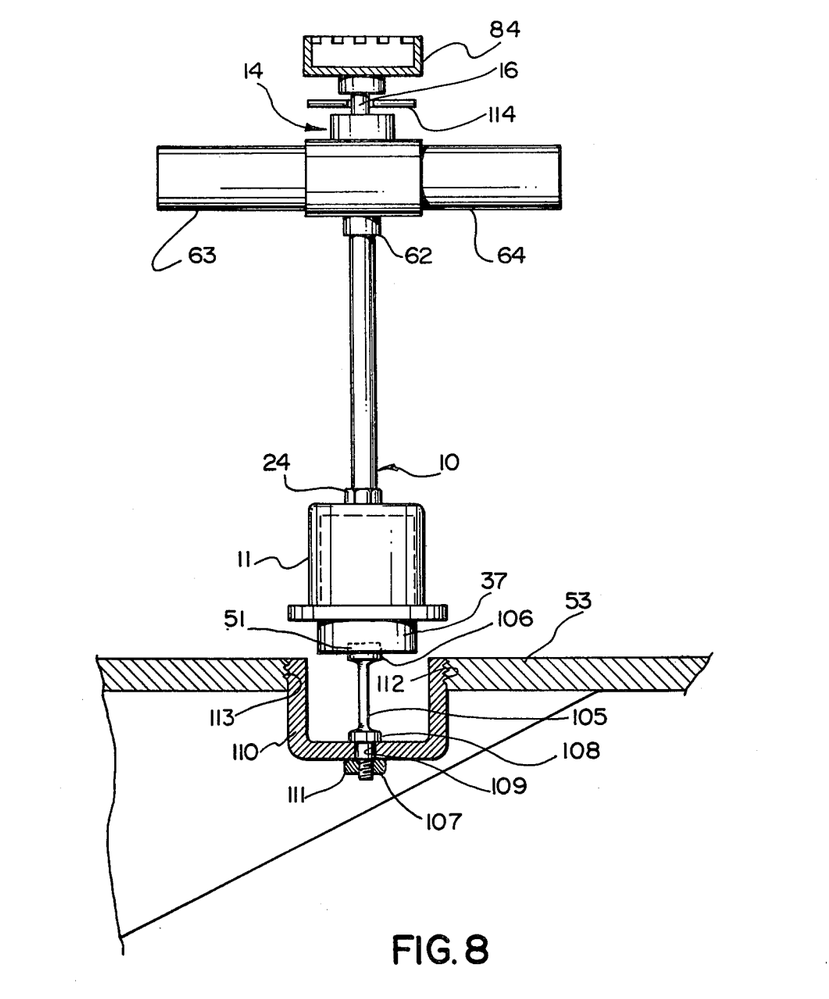
FIG. 8 is a side elevation of the densimeter spindle showing a modified form of resilient mounting connecting the spindle to the apparatus frame, in which the same reference numerals are used to indicate parts also used in the first example.

Instead of providing an upper bearing assembly 77 which is resiliently mounted to the apparatus frame by the arrangement of FIG. 3, and instead of pivotally mounting the lower seal housing 37 to the apparatus frame by the arrangement shown in FIG. 2, a modified resilient mounting as shown in FIG. 8 may be used without an upper bearing assembly.

The modified resilient mounting comprises a flexure shaft or bar 105 made of spring steel. The shaft 105 has at one end an increased diameter portion 106 which is secured in force-fit in the recess 51 of the lower seal housing 37. The shaft 105 is threaded at its other end 107 and is provided with a flange or collar 108 a short distance inwardly of the threaded end 107.

The threaded end 107 is received through a hole 109 in the bottom of a vertically disposed cylindrical mounting member 110 which is open at the top. The collar 108 limits downward movement of the shaft 105 and a nut 111 secured to the threaded end 107 secures the shaft 105 to the member 110.

The upper portion of the member 110 is threaded at 112 and is threadably secured in a mating hole 113 provided in the portion 53 of the base housing 31.

According to this modification the shaft 16 at the upper end of the densimeter spindle is not supported in bearings but is left unsupported. The drum 84 is connected to the free end of the shaft 16 as before. An oversized bushing 114 positioned at the shaft 16 and rigidly mounted in the frame by means now shown permits an amount of lateral movement of the shaft 16 and drum 84 corresponding to the greatest deflection for which the device is designed. The bushing 114 prevents lateral deflection beyond this point, thus protecting the spindle and, in particular, the shaft 105 from damage.

The operation of the device is identical to that of the previously described example except that lateral oscillation of the system is permitted solely by lateral flexure of the flexure shaft 105.

This modification thus obviates the requirement for an upper bearing and a resilient mounting for the upper bearing.

It has been found that, because of heat transfer through the outer wall of the half 64 of the rotor tube 15, the temperature sensed by the temperature sensor 103 may not be identical with the actual temperature of the fluid in the rotor half 64, tending to reduce the accuracy of the device. A simple way of overcoming this problem is to provide the rotor tube 15, which is preferably made of steel, with an outer covering of thermal insulating material extending at least over the half 64 of the rotor 15.

What we claim as our invention is:

1. A densimeter comprising a substantially vertical shaft having a central axis, means for rotating the shaft about its axis, a vessel for containing a liquid sample mounted on the shaft asymmetrically with respect to the shaft axis, counterbalancing means for at least partly compensating for the asymmetry, the shaft being resiliently mounted with freedom of oscillation transverse to the axis, and means for measuring the amplitude of the oscillations, said measuring means including two radiation paths each of which comprises a source and a detector, a shutter carried by the shaft and disposed to interrupt the radiation paths to generate two waveforms as the shaft rotates and means for detecting a shift in phase between the two waveforms, whereby the phase shift is proportional to the amplitude of the oscillations which, in turn, is proportional to the deviation of the specific gravity of the sample from a reference value.

2. A densimeter as claimed in claim 1, in which the radiation paths are light paths.

3. A densimeter as claimed in claim 2, in which the shutter is a drum having a flange with a plurality of slots.

4. A densimeter as claimed in claim 2, in which the radiation sources are disposed adjacent the axis of the shaft and the radiation detectors are disposed at locations diametrically opposed with respect to the shaft axis.

5. A densimeter as claimed in claim 1, in which the radiation detectors derive electrical waveforms corresponding to the radiation waveforms, the outputs of the detectors being fed to a phase comparator.

6. A densimeter as claimed in claim 5, including means for generating a reference signal at a frequency corresponding to the speed of rotation of the shaft, and means for feeding the reference signal together with the output from the phase comparator to a synchronous detector, the output of the synchronous detector being a full wave rectified signal corresponding to the amplitude of the oscillations.

7. A densimeter as claimed in claim 6, including a temperature sensor for deriving a voltage porportional to the temperature of the sample, and a function generator fed by the temperature sensor and deriving an output which is a function of the input corresponding to the function relationship between the density and the temperature of the sample, the output of the function generator being fed to a summer together with the filtered output of the synchronous detector.

8. A densimeter as claimed in claim 7, in which the vessel is provided with an outer covering of thermal insulating material.

9. A densimeter as claimed in claim 1, in which the shaft is hollow and the vessel comprises two adjacent compartments extending laterally and communicating at their end remote from the shaft, each compartment having a hole communicating with the interior of the shaft, and including means for pumping continuously fluid via the shaft serially through the two compartments.

10. A densimeter as claimed in claim 9, in which the shaft comprises two spaced concentric tubes the inner of which communicates with one of the compartments and the space between the concentric tubes communicating with the other compartment, whereby the outlet flow of fluid along the shaft is counter to and separate from the inlet flow.

11. A densimeter as claimed in claim 10, in which the inner tube has air bleed holes adjacent the vessel to permit air bubbles to circumvent the vessel.

12. A densimeter as claimed in claim 10 in which the lower end of the inner tube communicates with a first hose for feeding or exhausting and the lower end of the outer tube is provided with circumferentially spaced holes communicating with a second hose for feeding or exhausting.

13. A densimeter as claimed in claim 1, in which the vertical shaft is rotatably supported at a lower end portion by means of a bearing assembly and is unsupported over the remainder of the shaft, the bearing assembly being secured to a fixed frame member by means of a flexible member.

14. A densimeter as claimed in claim 13, in which the flexible member is a metal bar substantially vertically aligned with the rotatable shaft and connected at its upper end to the bearing assembly and at its lower end to the fixed frame member.

15. A continuous flow densimeter comprising a substantially vertical shaft having a central axis, means for rotating the shaft about the central axis, a vessel mounted on the shaft asymmetrically with respect to the shaft axis, counterbalancing means on the shaft for at least partly compensating for the asymmetry, the shaft being resiliently mounted with freedom of oscillation transverse to the shaft axis, and means for measuring the amplitude of the oscillations, the shaft comprising two concentric tubes, the inner tube communicating with the interior of the vessel, and the space between the two tubes communicating with the interior of the vessel, the shaft being adapted to permit fluid to be pumped through the vessel via the shaft whereby the outlet flow of fluid along the shaft is counter to and separate from the inlet flow.

16. A densimeter as claimed in claim 15, in which the vertical shaft is rotatably supported at a lower end portion by means of a bearing assembly and is unsupported over the remainder of the shaft, the bearing assembly being secured to a fixed frame member by means of a flexible member.

17. A densimeter as claimed in claim 16, in which the flexible member is a metal bar substantially vertically aligned with the rotatable shaft and connected at its upper end to the bearing assembly and at its lower end to the fixed frame member.